US011944756B2

(12) United States Patent
Gammon

(10) Patent No.: US 11,944,756 B2
(45) Date of Patent: Apr. 2, 2024

(54) OXYGEN SOURCE ATTACHMENT FOR A TRACHEAL DEVICE

(71) Applicant: Claudine Gammon, Richmond, CA (US)

(72) Inventor: Claudine Gammon, Richmond, CA (US)

( * ) Notice: Subject to any disclaimer, the term of this patent is extended or adjusted under 35 U.S.C. 154(b) by 642 days.

(21) Appl. No.: 17/013,205

(22) Filed: Sep. 4, 2020

(65) Prior Publication Data

US 2021/0069449 A1 Mar. 11, 2021

Related U.S. Application Data

(60) Provisional application No. 62/897,097, filed on Sep. 6, 2019.

(51) Int. Cl.
*A61M 16/10* (2006.01)
*A61M 16/04* (2006.01)
*A61M 16/08* (2006.01)
*A61M 16/22* (2006.01)

(52) U.S. Cl.
CPC .... *A61M 16/1005* (2014.02); *A61M 16/0465* (2013.01); *A61M 16/0816* (2013.01); *A61M 16/0875* (2013.01); *A61M 16/22* (2013.01); *A61M 2202/0208* (2013.01)

(58) Field of Classification Search
CPC .......... A61M 16/0472; A61M 16/0891; A61M 16/0463; A61M 16/0448; A61M 39/22; A61M 16/00; A61M 16/04–0402; A61M 16/0461; A61M 16/0465–0468; A61M 16/0475–0477; A61M 16/08; A61M 16/0816; A61M 16/0875; A61M 16/10–101; A61M 16/20–201; A61M 2202/0208
See application file for complete search history.

(56) References Cited

U.S. PATENT DOCUMENTS

| | | | |
|---|---|---|---|
| 3,066,674 A * | 12/1962 | Capra | A61M 16/0468 623/9 |
| 4,683,879 A | 8/1987 | Williams | |
| 4,919,127 A | 4/1990 | Pell | |
| 5,285,776 A | 2/1994 | Bertram | |
| D362,718 S | 9/1995 | Deily et al. | |
| 5,579,762 A | 12/1996 | Lee | |
| 7,059,322 B2 | 6/2006 | Rich et al. | |
| D551,344 S | 9/2007 | Santora, Jr. et al. | |
| D655,411 S | 3/2012 | Schroeder et al. | |
| 8,226,632 B2 | 7/2012 | Zawacki et al. | |
| 8,316,845 B2 | 11/2012 | Tappehorn et al. | |
| 8,905,030 B2 | 12/2014 | Stephenson et al. | |
| D736,914 S | 8/2015 | Schultz | |

(Continued)

*Primary Examiner* — Rachel T Sippel
(74) *Attorney, Agent, or Firm* — Vierra Magen Marcus LLP

(57) ABSTRACT

A tracheal tube attachment for a tracheal device is disclosed. The tracheal tube attachment fits over an end of a tracheal device to directly connect the tracheal device to an oxygen source. The tracheal tube attachment may include a central chamber having radial openings which may be partially or fully covered by a collar rotatably fitted around the central chamber. The collar and radial openings may be used to control the amount of oxygen received through the oxygen tube, as well as exhaling carbon dioxide to ambient.

14 Claims, 4 Drawing Sheets

(56) References Cited

U.S. PATENT DOCUMENTS

| | | | |
|---|---|---|---|
| 2005/0199243 A1* | 9/2005 | Svendsen | A61M 16/0463 |
| | | | 128/207.14 |
| 2008/0041391 A1* | 2/2008 | Worley | A61M 16/0816 |
| | | | 128/207.14 |
| 2012/0006330 A1* | 1/2012 | Barbot | A61M 16/0465 |
| | | | 128/207.14 |
| 2014/0366880 A1* | 12/2014 | Metz | A61M 16/127 |
| | | | 128/204.25 |
| 2016/0074610 A1 | 3/2016 | Rubin | |
| 2019/0070376 A1* | 3/2019 | Ferrer | A61M 16/0816 |
| 2019/0290876 A1* | 9/2019 | Fuller | A61M 16/0497 |

* cited by examiner

OXYGEN SOURCE ATTACHMENT FOR A TRACHEAL DEVICE

PRIORITY CLAIM

The present application claims priority to U.S. Provisional Patent Application No. 62/897,097, filed on Sep. 6, 2019, entitled "OXYGEN SOURCE ATTACHMENT FOR A TRACHEAL DEVICE," which application is incorporated by reference herein in its entirety.

BACKGROUND

Diseases such as larynx cancer can lead to an obstruction in the nose, mouth, or the upper portion of the windpipe, making it difficult for a person to breathe. In these cases, it may be necessary to create a by-pass air passageway in the person's neck using a tracheal device, such as a tracheostomy tube. The tracheostomy tube is inserted through a stoma in the person's neck and into the trachea to connect the trachea with air outside the person's body.

On occasion, it is necessary or desirable to connect a tracheal tube patient to an oxygen concentrator, tank or other oxygen source. Currently, this is done by attaching the oxygen tube from the oxygen source to a larger diameter tube, which is then attached to a large mask that is strapped around the patient's neck. This is an inefficient way to deliver oxygen, and can also result in patient discomfort.

SUMMARY

The present technology provides a new and improved solution to numerous problems experienced by persons with tracheal devices. A basic concept of the present technology is to provide a tracheal tube attachment for a tracheal device. The attachment receives oxygen directly from an oxygen source, such as an oxygen concentrator, tank or other oxygen source.

The tracheal tube attachment essentially comprises central chamber having a proximal end and a distal end. The proximal end is configured to press-fit over an end of the tracheal tube to provide an air-tight seal with the tracheal tube. The distal end is closed, except for a reduced-diameter end section configured to press-fit within an end of a flexible oxygen tube to provide an air-tight seal with the oxygen tube. The central chamber may comprise radial openings and a collar rotationally mounted over the central chamber and capable of rotating between positions where the collar covers (or partially covers) the radial openings, and positions where the collar does not cover the radial openings. The collar and radial openings may be used to control the amount of oxygen received through the oxygen tube, as well as exhaling carbon dioxide to ambient.

DETAILED DESCRIPTION

The present technology includes a tracheal tube attachment used by a person having a tracheal device, such as a tracheostomy tube, fitted through a stoma in the person's neck and extending into the person's trachea. In embodiments described below, the tracheal tube attachment fits over an end of a tracheal device to directly connect the tracheal device to an oxygen source. The tracheal tube attachment may include a central chamber having radial openings which may be partially or fully covered by a collar rotatably fitted around the central chamber. The collar and radial openings may be used to control the amount of oxygen received through the oxygen tube, as well as exhaling carbon dioxide to ambient.

The terms "top" and "bottom," "upper" and "lower" and "vertical" and "horizontal," and forms thereof, as may be used herein are by way of example and illustrative purposes only, and are not meant to limit the description of the present technology inasmuch as the referenced item can be exchanged in position and orientation. Also, as used herein, the terms "substantially" and/or "about" mean that the specified dimension or parameter may be varied within an acceptable manufacturing tolerance for a given application. In one embodiment, the acceptable manufacturing tolerance is ±2.5%.

Figure 1:
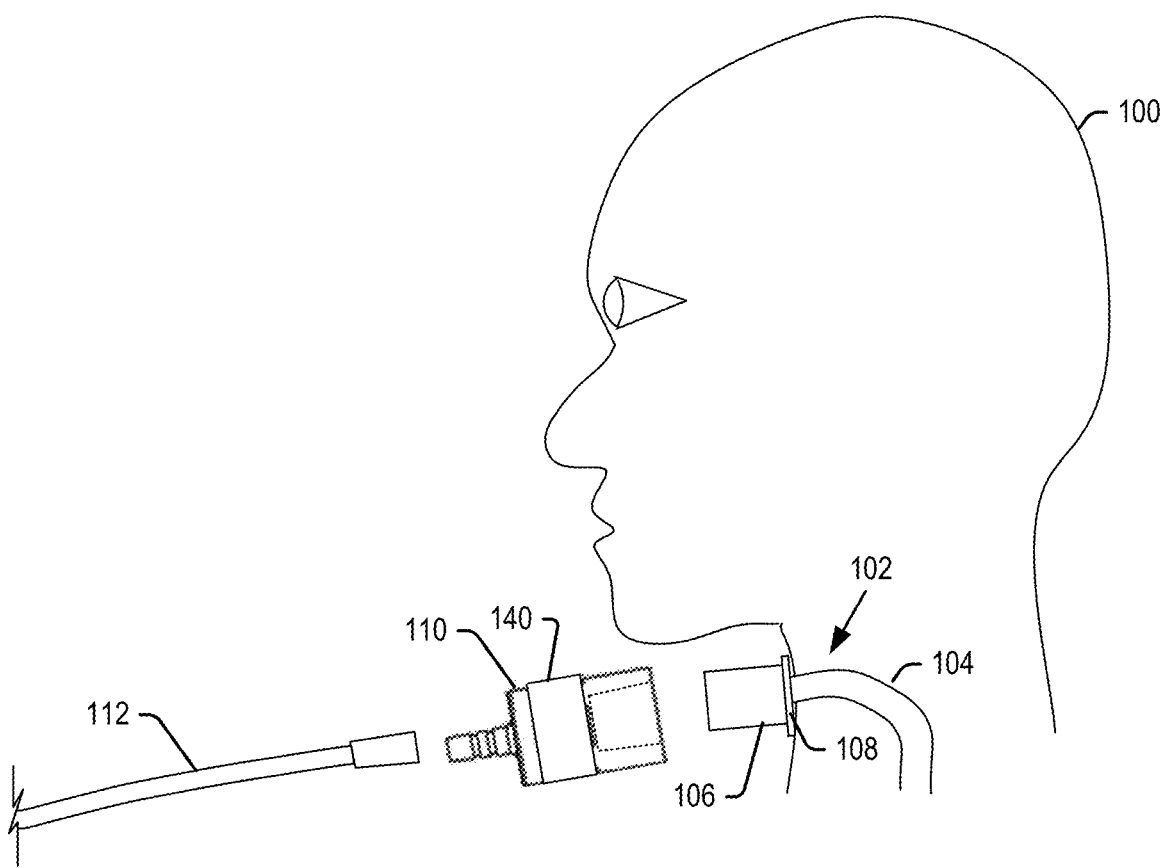
FIG. 1 is a side view of a tracheal tube attachment and a tracheal device in a patient in a patient.
Figure 2:
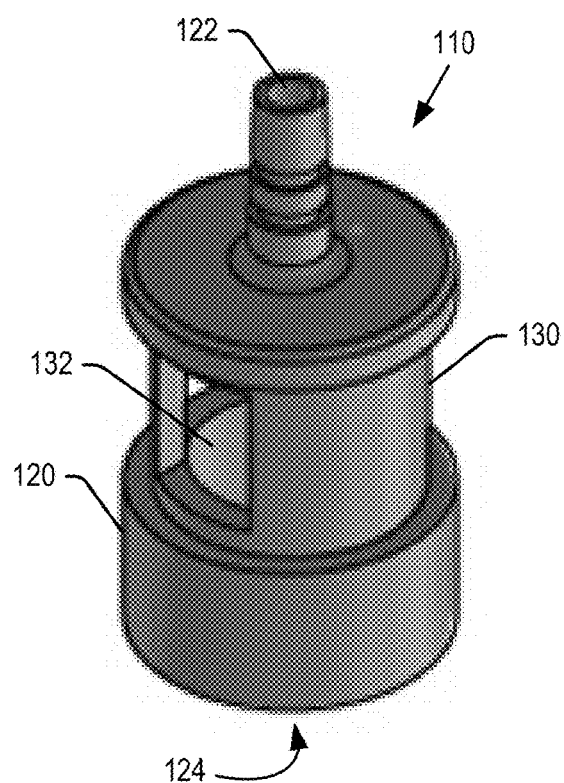
FIG. 2 is a perspective view of a tracheal tube attachment according to embodiments of the present technology.
Figure 3:
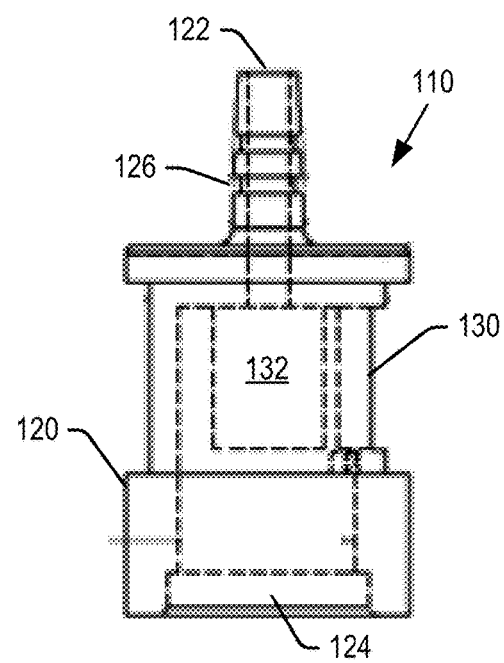
FIG. 3 is a side view of a tracheal tube attachment according to embodiments of the present technology.
Figure 4:
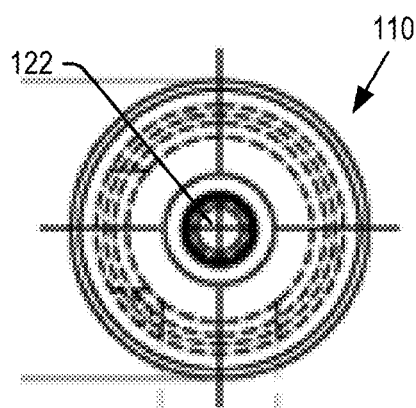
FIG. 4 is a top view of a tracheal tube attachment according to embodiments of the present technology.
Figure 5:
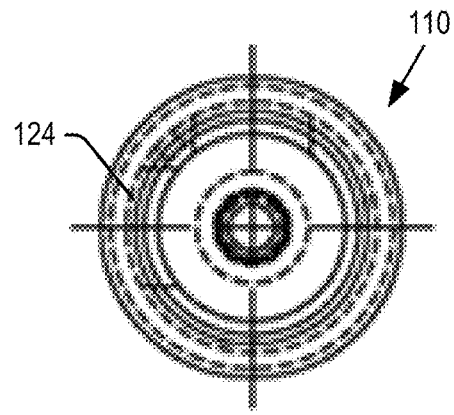
FIG. 5 is a bottom view of a tracheal tube attachment according to embodiments of the present technology.

Referring now to FIG. 1, there is shown a patient 100 including a tracheal device 102 and a tracheal tube attachment 110 according to embodiments of the present technology. The tracheal device 102 may consist of a cannula 104 fitted within a person's trachea and extending out of a stoma in the person's neck. A distal end of the cannula 104 may include a cap 106 external to the person's body, and held in place by a plate 108.

The tracheal tube attachment 110 is configured to allow a flexible air hose 112 to supply a gas such as oxygen directly to the tracheal device 102. The air hose 112 to be connected to a gas source (not shown), such as for example an oxygen concentrator, an oxygen tank or a wall mount to an oxygen supply. The tracheal to attachment 110, including collar 140 (explained below), may be made from medical grade ABS plastic and/or a thermoplastic such as nylon, polyethylene or polypropylene, although it is understood that other materials may be used in further embodiments.

Referring now to FIGS. 2-5, in order to connect air hose 112 to tracheal device 102, the tracheal tube attachment 110 includes a central body 120 having a hollow interior connected at a first (distal) end to an air hose connector 122 and at a second (proximal) end to a cap connector 124. The air hose connector 122 may be sized and shaped to connect within an end of the air hose 112 with a firm frictional fit. The air hose connector 122 may include recesses 126 (FIG. 3) in an outer surface of the connector 122 to facilitate the frictional fit. It is understood that air hose connector 122 may be removably attached to an end of the air hose by a wide variety of other fastening schemes in further embodiments. In one such further embodiment, the air hose connector 122 may have a larger diameter than shown, so that the end of the air hose 112 fits within an interior of the air hose connector 122.

The cap connector 124 may be sized and shaped to connect over the cap 106 with a firm frictional fit. It is understood that cap connector 124 may be removably attached to the cap 106 by a wide variety of other fastening schemes in further embodiments. In one such further embodiment, the cap connector 124 may have a smaller diameter than shown, so that the cap connector 124 fits within an interior of the cap 106. When the air hose connector 122 is attached to air hose 112, and the cap connector 124 is attached to the cap 106, oxygen or other gases within air hose 112 may flow directly into the tracheal device 110. This arrangement provides for a relatively unobstructed turbulent free flow of gas with a minimal effort by the patient, and further omits the need for a mask.

The central portion 120 of the tracheal tube attached 110 may have a constant diameter along its length, except for a reduced diameter section 130 configured to receive a collar 140 (explained below). The reduced diameter section 130 includes one or more radial openings 132 formed in the outer diameter of the reduced diameter section 130, which openings 132 open an interior of the central portion 120 to the ambient environment surrounding the tracheal tube attachment 110. The number and sizes of the radial openings 132 may vary, but in one embodiment, there may be two such radial openings extending around a 180° arc length of the reduced diameter section 130.

Figure 6:
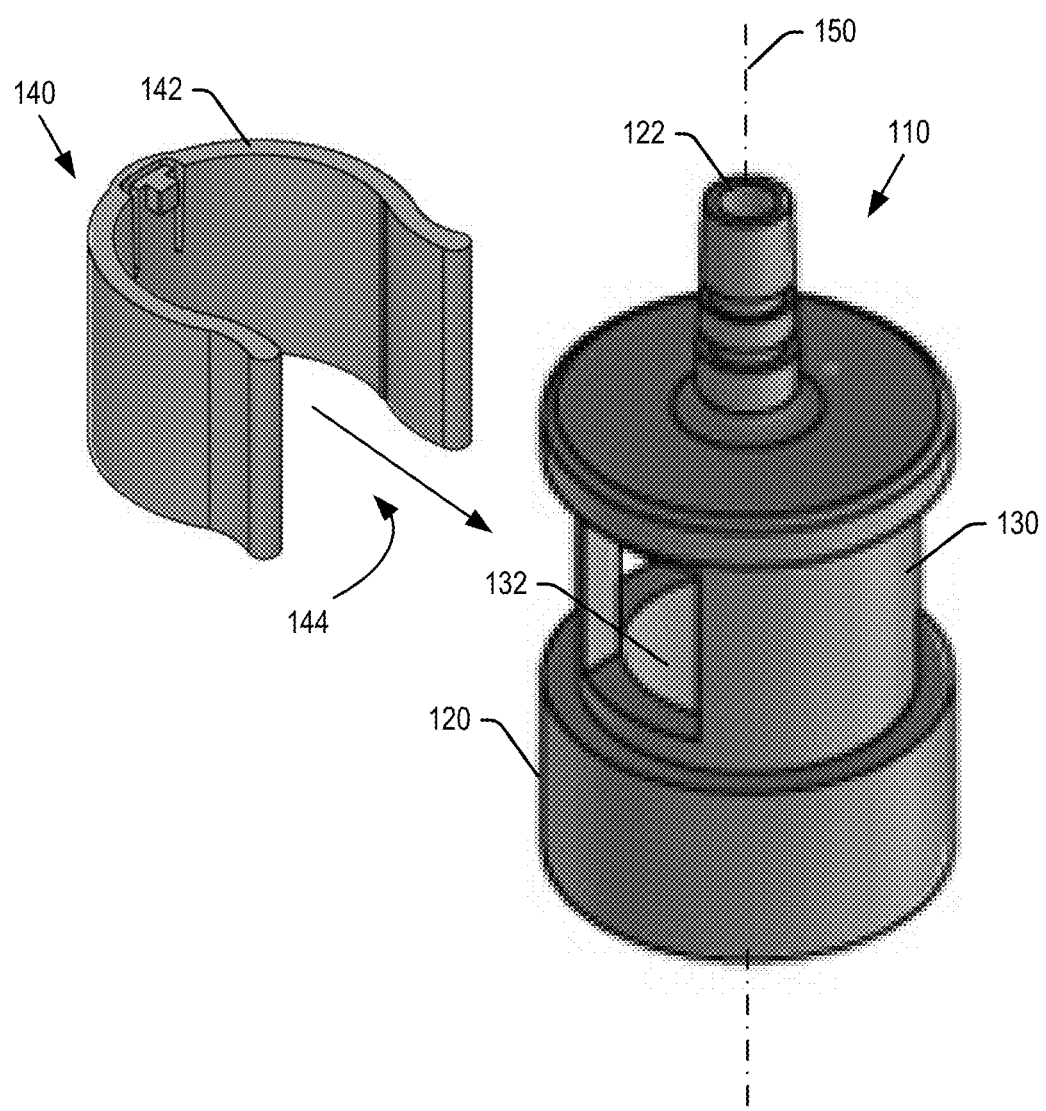
FIG. 6 is an exploded perspective view of a tracheal tube attachment and collar according to embodiments of the present technology.

Referring now to the exploded perspective view of FIG. 6, a collar 140 may snap fit over the reduced diameter section 130 so as to be able to rotate around the reduced diameter section 130. The collar is semicircular so as to include a solid section 142 and an open section 144. The collar 140 may be snap fit over the reduced diameter section 130 by inserting the open section 144 around the reduced diameter section 130. Once mounted around the reduced diameter section 130, the collar 140 may rotate around a central axis 150 of the tracheal tube attachment 110. As the collar 140 rotates, the solid section 142 may cover the radial openings 132. In this "closed" position, little or no ambient air mixes with the incoming oxygen, and the patient receives a high concentration of oxygen. As the collar rotates, the open section 144 may alternatively align with the radial openings 132. In this "open" position, a high degree of ambient air mixes with the incoming oxygen, and the patient receives a lower concentration of oxygen. The solid section 142 may also partially cover one or more of the radial openings 132, such that the central section may be "partially open" by a controlled amount to control the level of ambient air allowed to enter the interior of the tracheal tube attachment 110.

Moreover, the collar 140 and radial openings 132 may be positioned relative to each other to control the amount of exhaled carbon dioxide vented through the tracheal tube attachment 110. For example, where a person is still able to exhale (at least to some degree) through their mouth or nose, the collar 140 may cover the radial openings 132. In this instance, the person receives a high concentration of oxygen, while venting carbon dioxide through their mouth or nose. Where the person is not able to exhale through their mouth or nose, the collar 140 may leave all or a portion of the radial openings 132 uncovered, so that some ambient air is taken in while inhaling, but exhaled carbon dioxide is able to vent to ambient through the radial openings 132. The amount by which the collar 140 covers the radial openings may be set by the user based on the amount of oxygen they need versus the amount of carbon dioxide they need to vent through the tracheal tube attachment 110.

Once rotated to a desired position, the collar 140 may stay in place due to a frictional fit between the collar 140 in the reduced diameter section 130. It is understood that the collar 140 may be affixed to the central portion 120 by other mechanical arrangements, including for example a circular rack on one of the central portion 120 and collar, and a pinion gear on the other of the central portion 120 and collar.

Figure 7:
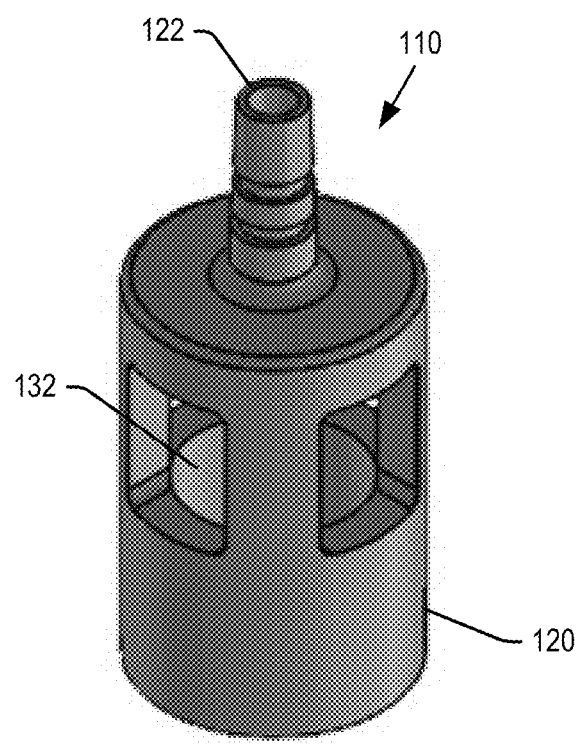
FIG. 7 is a perspective view of a tracheal tube attachment according to an alternative embodiment of the present technology.

FIG. 7 shows a further embodiment where the reduced diameter section 130 and collar 140 may be omitted. In this embodiment, the central section 120 may be in a permanently open position, allowing air into the interior of the central opening and allowing carbon dioxide to vent to ambient.

One skilled in the art will recognize that the Internet service may be configured to provide Internet access to one or more computing devices that are coupled to the Internet service, and that the computing devices may include one or more processors, buses, memory devices, display devices, input/output devices, and the like. Furthermore, those skilled in the art may appreciate that the Internet service may be coupled to one or more databases, repositories, servers, and the like, which may be utilized in order to implement any of the embodiments of the invention as described herein.

I claim:

1. A tracheal tube attachment for a tracheal device comprising:
    a first end configured to attach to an air hose;
    a second end configured to attach to the tracheal device;
    a central section comprising a longitudinal axis and one or more radial openings; and
    a semicircular collar configured to fit around a portion of the central section to cover, partially cover or leave uncovered the one or more radial openings, the collar configured to fit on the central section in a direction perpendicular to the longitudinal axis of the central section.

2. The tracheal tube attachment as set forth in claim 1, wherein the central section has a consistent diameter along its length, except for a reduced diameter section configured to receive the collar.

3. The tracheal tube attachment as set forth in claim 1, wherein a diameter of the first end dimensioned to fit within the air hose.

4. The tracheal tube attachment as set forth in claim 1, wherein the first end is configured for a frictional fit within the air hose.

5. The tracheal tube attachment as set forth in claim 1, wherein a diameter of the second end dimensioned to fit around a cap of the tracheal device.

6. The tracheal tube attachment as set forth in claim 1, wherein the second end is configured for a frictional fit around a cap of the tracheal device.

7. The tracheal tube attachment as set forth in claim 1, wherein the one or more radial openings comprise two radial openings.

8. A tracheal tube attachment for a tracheal device comprising:
    a first end configured to attach to an air hose;
    a second end configured to attach to the tracheal device;
    a central section comprising a cylindrical shape having a longitudinal axis and one or more radial openings; and
    a collar configured to rotate around a portion of the central section over the one or more radial openings, the collar being semicircular to have an open section, the collar configured to fit on the central section in a direction perpendicular to the longitudinal axis of the central section, wherein the open section of the collar is configured to be rotated to a position relative to the radial openings based on an amount of carbon dioxide needed to be vented through the tracheal tube attachment.

9. The tracheal tube attachment as set forth in claim 8, wherein the collar is positioned relative to the one or more radial openings in one of an open position, a partially open position or a closed position.

10. The tracheal tube attachment as set forth in claim 8, wherein the collar completely covers the one or more radial openings to maximize an amount of oxygen received through the tracheal tube attachment and minimizing an amount of carbon dioxide vented through the one or more radial openings.

11. The tracheal tube attachment as set forth in claim 8, wherein the one or more radial openings are completely uncovered by the collar to minimize an amount of oxygen received through the tracheal tube attachment and maximizing an amount of carbon dioxide vented through the one or more radial openings.

12. The tracheal tube attachment as set forth in claim 8, wherein the first end is configured for a frictional fit within the air hose.

13. The tracheal tube attachment as set forth in claim 8, wherein the second end is configured for a frictional fit around a cap of the tracheal device.

14. The tracheal tube attachment as set forth in claim 8, wherein the one or more radial openings comprise two radial openings.

* * * * *